(12) United States Patent
Dybajlo et al.

(10) Patent No.: US 12,414,970 B2
(45) Date of Patent: Sep. 16, 2025

(54) ***BACILLUS* COAGULANS AND *BACILLUS SUBTILIS* FOR THE PREVENTION AND TREATMENT OF FUNCTIONAL GASTRO-INTESTINAL DISORDERS**

(71) Applicant: MY RESEARCH, Lummen (BE)

(72) Inventors: Raf Dybajlo, Lummen (BE); Wannes Thys, Bilzen (BE); Lucas Wauters, Leuven (BE); Tim Vanuytsel, Leuven (BE)

(73) Assignee: My Health International, Diepenbeek (BE)

( * ) Notice: Subject to any disclaimer, the term of this patent is extended or adjusted under 35 U.S.C. 154(b) by 736 days.

(21) Appl. No.: 17/599,104

(22) PCT Filed: Mar. 27, 2020

(86) PCT No.: PCT/EP2020/058850
§ 371 (c)(1),
(2) Date: Sep. 28, 2021

(87) PCT Pub. No.: WO2020/201153
PCT Pub. Date: Oct. 8, 2020

(65) Prior Publication Data
US 2022/0160793 A1    May 26, 2022

(30) Foreign Application Priority Data

Mar. 29, 2019    (BE) .................................. 2019/5201

(51) Int. Cl.
*A61P 1/00* (2006.01)
*A23L 2/52* (2006.01)
(Continued)

(52) U.S. Cl.
CPC .............. *A61K 35/742* (2013.01); *A23L 2/52* (2013.01); *A23L 33/135* (2016.08); *A23L 33/40* (2016.08);
(Continued)

(58) Field of Classification Search
CPC ....... A61K 35/742; A23L 33/135; A61P 1/14; A61P 1/00
See application file for complete search history.

(56) References Cited

FOREIGN PATENT DOCUMENTS

| CN | 101926831 A | * | 12/2010 |
| JP | 2017109973 A | * | 6/2017 |
| RU | 2437563 C1 | | 12/2011 |

OTHER PUBLICATIONS

Klaire Labs Biospora Probiotic—Bacillus Coagulans & Subtilis 2 Billion CFU for Digestive & Immune Support—Soil-Based (SBO) & Shelf-Stable Spore Forming Probiotic for Men & Women (120 Capsules), www.amazon.com/Klaire-Labs-Biospora-Coagulans-Probiotics/dp/B00IO5A3T6, 2013 (Year: 2013).*

(Continued)

*Primary Examiner* — Louise W Humphrey
*Assistant Examiner* — Mary A Crum
(74) *Attorney, Agent, or Firm* — Dinsmore & Shohl LLP (57) ABSTRACT

The invention in general relates to the use of probiotics for the management of functional gastrointestinal disorders. More specifically, the present invention relates to the use of *Bacillus coagulans* or *Bacillus subtilis* or a combination of both strains for the prevention or treatment of functional gastrointestinal disorders, such as for example functional dyspepsia. The present invention also discloses the use of *Bacillus coagulans* or *Bacillus subtilis* or a combination of both strains as alternative therapy or adjunct therapy for or gastric acid suppression treatment.

13 Claims, 4 Drawing Sheets

(51) Int. Cl.
*A23L 33/00* (2016.01)
*A23L 33/135* (2016.01)
*A61K 35/742* (2015.01)
*A61K 45/06* (2006.01)
*A61P 1/14* (2006.01)
*A61K 35/00* (2006.01)

(52) U.S. Cl.
CPC .............. *A61K 45/06* (2013.01); *A61P 1/14* (2018.01); *A23V 2002/00* (2013.01); *A61K 2035/115* (2013.01)

(56) References Cited

OTHER PUBLICATIONS

Talley, N. J., and K. Lauritsen. "The potential role of acid suppression in functional dyspepsia: the Bond, Opera, Pilot, and Encore studies." Gut 50.suppl 4 (2002): iv36-iv41. (Year: 2002).*
Kalman, Douglas S., et al. "A prospective, randomized, double-blind, placebo-controlled parallel-group dual site trial to evaluate the effects of a Bacillus coagulans-based product on functional intestinal gas symptoms." BMC gastroenterology 9 (2009): 1-7 (Year: 2009).*
Pilin Francis, Zavala SR. Functional Dyspepsia. [Updated Jun. 8, 2024]. In: StatPearls [Internet]. Treasure Island (FL): StatPearls Publishing; Jan. 2024 (Year: 2024).*
Hatanaka, M., et al. "Effect of Bacillus subtilis C-3102 on loose stools in healthy volunteers." Beneficial microbes 9.3 (2018): 357-365. (Year: 2018).*
Cleveland Clinic, Functional Dyspepsia, 2022, my.clevelandclinic.org/health/diseases/22248-functional-dyspepsia (Year: 2022).*
International Search Report and Written Opinion mailed Jun. 19, 2020, in reference to co-pending European Patent Application No. PCT/EP2020/058850 filed Mar. 27, 2020.
Boghossian, et al., "Deprescribing versus continuation of chronic proton pump inhibitor use in adults (Review)", The Cochrane Collaboration, pp. 1-4, 2017.
Cirillo, et al., "Evidence for Neuronal and Structural Changes in Submucous Ganglia of Patients with Functional Dyspepsia", American Journal of Gastroenterology, pp. 1205-1215, 2015.
Cutting, "Bacillus Probiotics", Food Microbiology, vol. 28, pp. 214-220, 2011.
Elshaghabee, et al., "Bacillus As Potential Probiotics: Status, Concerns, and Future Perspectives", Frontiers in Microbiology, vol. 8, Article 1490, pp. 1-15, Aug. 10, 2017.
Igarashi, et al., "Alteration in the gastric microbiota and its restoration by probiotics in patients with functional dyspepsia", BMJ Open Gastro, pp. 1-9, 2017.
Jackson, et al., "Proton pump inhibitors alter the composition of the gut microbiota", BMJ, vol. 65, pp. 749-756, 2016.
Kindt, et al., "Immune dysfunction in patients with functional gastrointestinal disorders", Neurogastroenterol Motil, vol. 21, pp. 389-398, 2009.
Lo, et al., "Systematic Reviews and Meta-Analyses", Clinical Gastroenterology and Hepatology, vol. 11, pp. 483-490, 2013.
Moayyedi, et al., "ACG and CAG Clinical Guideline: Management of Dyspepsia", The American Journal of Gastroenterology, vol. 112, pp. 988-1013, Jul. 2017.
Sterbini, et al., "Effects of Proton Pump Inhibitors on the Gastric Mucosa-Associated Microbiota in Dyspeptic Patients", Applied and Environmental Microbiology, vol. 82, No. 22, pp. 6633-6644, Nov. 2016.
Pinto-Sanchez, et al., "Proton pump inhibitors for functional dyspepsia (Review)", The Cochrane Collaboration, pp. 1-4, 2017.
Stanghellini, et al., "Gastroduodenal Disorders", Gastroenterology, vol. 150, No. 6, pp. 1380-1392, May 2016.
Talley, et al., "Functional Dyspepsia", The New England Journal of Medicine, pp. 1853-1863, Nov. 5, 2015.
Tsuda, et al., "Influence of Proton-Pump Inhibitors on the Luminal Microbiota in the Gastrointestinal Tract", Clinical and Translational Gastroenterology, vol. 6, N. 10, pp. 1-9, 2015.
Vanheel, et al., "Impaired duodenal mucosal integrity and low-grade inflammation in functional dyspepsia", Neurogastroenterology, pp. 262-272, 2014.
Vanuytsel, et al., "Psychological stress and corticoticotropin-releasing hormone increase intestinal permeability in humans by a mast cell-dependent mechanism", Neurogastroenterology, vol. 63, pp. 1293-1299, 2014.
Zhong, et al., "Dyspepsia and the microbiome: time to focus on the small intestine", BMJ, vol. 66, No. 6, pp. 1168-1170—Jun. 2017.

* cited by examiner

BACILLUS COAGULANS AND BACILLUS SUBTILIS FOR THE PREVENTION AND TREATMENT OF FUNCTIONAL GASTRO-INTESTINAL DISORDERS

CROSS-REFERENCE TO RELATED APPLICATIONS

This application is a § 371 national stage entry of PCT/EP2020/058850, filed Mar. 27, 2020, which claims priority to BE2019/5201, filed Mar. 29, 2019, the entire contents of which are incorporated herein by reference in their entirety.

FIELD OF THE INVENTION

The invention in general relates to the use of probiotics for the management of functional gastrointestinal disorders. More specifically, the present invention relates to the use of *Bacillus coagulans* or *Bacillus subtilis* or a combination of both strains for the prevention or treatment of functional gastrointestinal disorders, such as for example functional dyspepsia. The present invention also discloses the use of *Bacillus coagulans* or *Bacillus subtilis* or a combination of both strains as alternative therapy or adjunct therapy for gastric acid suppression treatment.

BACKGROUND TO THE INVENTION

Functional gastro-intestinal (GI) disorders, also known as disorders of the gut-brain interaction include a number of separate idiopathic disorders which affect different parts of the GI tract and involve visceral hypersensitivity and motility disturbances. Examples of functional GI disorders include functional dyspepsia, functional chest pain, functional heartburn, belching disorders, nausea and vomiting disorders, functional abdominal bloating or distension, reflux hypersensitivity, irritable bowel syndrome, functional constipation, functional diarrhea.

Functional dyspepsia is a functional GI disorder that refers to chronic or recurrent upper gastrointestinal (GI) symptoms originating from the gastroduodenal region with a significant impact on patients' lives (Talley N J et al. 2015. Functional Dyspepsia. *N Engl J Med* 373, 1853-63). Organic causes include peptic ulcer, *Helicobacter pylori* infection, biliary tract disease and esophagogastric cancers. According to the Rome criteria, functional dyspepsia (FD) comprises the diagnostic categories of epigastric pain syndrome (EPS) with epigastric pain or burning and postprandial distress syndrome (PDS) with meal-related fullness or early satiation, which are unexplained after routine investigation including upper GI endoscopy (Stanghellini V et al. 2016. Gastroduodenal Disorders. *Gastroenterology* 150, 1380-92). Despite the common occurrence of FD in up to 15% of the general population, the underlying pathophysiology remains unclear and the first-line treatment option is acid suppression (Moayyedi P M et al. 2017. ACG and CAG Clinical Guideline: Management of Dyspepsia. *Am J Gastroenterol* 112, 988-1013). Although gastro-esophageal reflux disease (GERD) may co-exist with FD, a population-based study from the Mayo Clinic concluded that FD is often underdiagnosed and mislabeled as GERD. A recent Cochrane-analysis concluded that proton pump inhibitors (PPI) are more effective in FD compared to placebo and histamine-2-receptor antagonists (Pinto-Sanchez M I et al. 2017. Proton pump inhibitors for functional dyspepsia. *Cochrane Database Syst Rev* 3, CD011194). However, PPIs are also associated with potential long-term adverse events such as an increased risk of GI infections and small intestinal bacterial overgrowth (Lo W et al. 2013. Proton Pump Inhibitor Use and the Risk of Small Intestinal Bacterial Overgrowth: A Meta-analysis. *Clin Gastroenterol Hepatol* 11, 483-90). Recent studies have also reported changes in both the gastric (Tsuda A et al. 2015. Influence of Proton-Pump Inhibitors on the Luminal Microbiota in the Gastrointestinal Tract. *Clin Trans Gastroenterol* 6, e89; Paroni Sterbini F et al. 2016. Effects of Proton Pump Inhibitors on the Gastric Mucosa-Associated Microbiota in Dyspeptic Patients. *App/Environ Microbiol* 82, 6633-44) and fecal (Jackson M A et al. 2016. Proton pump inhibitors alter the composition of the gut microbiota. *Gut* 65, 749-56; Imhann F et al. 2016. Proton pump inhibitors affect the gut microbiome. *Gut* 65, 740-8) microbiome during PPI treatment with an increase in oral flora, most likely resulting from the reduction of the gastric acid barrier and lack of bacterial killing in the acid-suppressed stomach. PPI may affect the gastric microbiome by increasing the relative abundance of *Streptococcus*, irrespective of the presence or absence of *H. pylori*, which may contribute to the persistence of FD symptoms with PPI or lead to long term adverse effects (Paroni Sterbini F et al. 2016. Effects of Proton Pump Inhibitors on the Gastric Mucosa-Associated Microbiota in Dyspeptic Patients. *Appl Environ Microbiol* 82, 6633-44). Moreover, inappropriate use of PPI puts a significant cost on the healthcare budget (Boghossian T A et al. 2017. Deprescribing versus continuation of chronic proton pump inhibitor use in adults. *Cochrane Database Syst Rev* 3, CD011969).

Several publications have demonstrated increased duodenal mucosal permeability and low-grade inflammation in FD patients, correlating with meal-related symptoms (Kindt S et al. 2009. Immune dysfunction in patients with functional gastrointestinal disorders. *Neurogastroenterol Motil* 21, 389-98; Vanheel H et al. 2014. Impaired duodenal mucosal integrity and low-grade inflammation in functional dyspepsia. *Gut* 63, 262-71; Cirillo C et al. 2015. Evidence for neuronal and structural changes in submucous ganglia of patients with functional dyspepsia. *Am J Gastroenterol* 110, 1205-15). The causes of the barrier defect and immune activation are unknown but candidates include psychological stress, luminal food components, (bile) acid and microbiota (Vanheel H et al. 2014. Impaired duodenal mucosal integrity and low-grade inflammation in functional dyspepsia. *Gut* 63, 262-71; Vanuytsel T et al. 2014. Psychological stress and corticotropin-releasing hormone increase intestinal permeability in humans by a mast cell-dependent mechanism. *Gut* 63, 1293-9). A preliminary report involving 9 FD patients showed an increase in *Streptococcus* and total bacterial load in the duodenal flora of FD compared to healthy controls, correlating with meal-related symptom severity and quality of life (Zhong L et al. 2017. Dyspepsia and the microbiome: time to focus on the small intestine. *Gut* 66, 1168-9).

Few clinical trials have tested probiotics for the treatment of functional dyspepsia. Recently, a probiotic treatment was found to be beneficial for postprandial dyspeptic symptoms (Igarashi M et al. 2017. Alteration in the gastric microbiota and its restoration by probiotics in patients with functional dyspepsia. BMJ open *Gastroenterol* 4, e000144), possibly through changes in the flora although this hypothesis was not tested in this study. *Bacillus* bacteria are gram positive strains capable of forming endospores which are highly resistant to gastric acid (Elshaghabee F M F et al. 2017. *Bacillus* As Potential Probiotics: Status, Concerns, and Future Perspectives. *Front Microbiol* 8, 1490). In addition, spore-forming probiotics or 'sporebiotics' are stable at room temperature and deliver more viable bacteria to the small intestine compared to traditional probiotic supplements (Cutting S M. 2011. *Bacillus* probiotics. *Food Microbiol* 28, 214-20). A combination of oral spore-based probiotics (*B. indicus, B. subtilis, B. coagulans, B. licheniformis* and *B. clausii*) was shown to reduce post-prandial endotoxemia, which may result from increased gut permeability (McFarlin B K et al. 2017. Oral spore-based probiotic supplementation was associated with reduced incidence of post-prandial dietary endotoxin, triglycerides, and disease risk biomarkers. *World J Gastrointest Pathophysiol* 8, 117-126).

The present invention describes the use of *Bacillus coagulans* or *Bacillus subtilis* or a combination of both strains for the prophylaxis and/or treatment of functional GI disorders, such as for example functional dyspepsia. Additionally the present invention also discloses the use of *Bacillus coagulans* or *Bacillus subtilis* or a combination of both strains as alternative therapy or adjunct therapy for gastric acid suppression treatment. In another aspect, the present invention discloses the use of *Bacillus coagulans* or *Bacillus subtilis* spores or a combination of both strains for the prevention or treatment of other diseases selected from metabolic syndrome, such as high cholesterol levels and high blood sugar levels; immune system disorders, such as chronic inflammation, allergies and auto-immune diseases; mental health disorders such as depression and anxiety; and urogenital disorders, such as urogenital infections.

SUMMARY OF THE INVENTION

The present invention describes the use of *Bacillus coagulans* or *Bacillus subtilis* or a combination of both strains for the prophylaxis/prevention and/or treatment of functional gastro-intestinal disorders in a subject. In particular, the invention is directed to a combination comprising *B. subtilis* and *B. coagulans* spores for use in the prevention and/or treatment of a functional gastro-intestinal (GI) disorder in a subject. Said functional GI disorder is selected from functional dyspepsia, functional chest pain, functional heartburn, belching disorders, nausea and vomiting disorders, functional abdominal bloating or distension, reflux hypersensitivity, irritable bowel syndrome, functional constipation, functional diarrhea. In a further embodiment, said functional GI disorder is selected from functional dyspepsia, functional chest pain, functional heartburn, belching disorders, nausea and vomiting disorders, functional abdominal bloating or distension. Thus, in an even more preferred embodiment, the present invention provides a combination comprising *B. subtilis* and *B. coagulans* spores for use in the prevention and/or treatment of functional dyspepsia in a subject.

Additionally the present invention discloses a combination comprising *B. subtilis* and *B. coagulans* spores for use as an alternative therapy or adjunct therapy for gastric acid suppression treatment in a subject, in particular in a subject with a functional gastro-intestinal (GI) disorder. Said functional GI disorder is selected from functional dyspepsia, functional chest pain, functional heartburn, belching disorders, nausea and vomiting disorders, functional abdominal bloating or distension, reflux hypersensitivity, irritable bowel syndrome, functional constipation, functional diarrhea. In a further embodiment, said functional GI disorder is selected from functional dyspepsia, functional chest pain, functional heartburn, belching disorders, nausea and vomiting disorders, functional abdominal bloating or distension. Thus, in an even more preferred embodiment, the present invention provides a combination comprising *B. subtilis* and *B. coagulans* spores for use as an alternative therapy or as an adjunct therapy for gastric acid suppression treatment in a subject, in particular in a subject with a functional gastro-intestinal (GI) disorder.

Further, in one aspect of the invention, a combination of *B. subtilis* and *B. coagulans* spores for use according to all the embodiments of the invention, is provided in combination with a standard therapy for functional gastro-intestinal disorders. In a further aspect, said standard therapy is selected from acid suppressive therapy (proton pump inhibitors and histamine-2 receptor antagonists), antibiotics, antiemetics, prokinetics, spasmolytics, antidepressants, antipsychotics, digestive enzymes and botanical extracts.

In another aspect of the invention, the combination for use according to the different embodiments of the present invention comprises *B. subtillis* and *B. coagulans* spores wherein said *B. subtilis* and *B. coagulans* spores are in a 1:1, a 1:2 or a 2:1 ratio.

In a further aspect, the combination for use according to the present invention comprises *B. subtilis* and *B. coagulans*, wherein said *B. subtilis* spores are derived from strain MY02 as deposited with the BCCM with accession number LMG P-31319. Said strain has been deposited with the Belgian Co-ordinated Collection of Micro-Organisms (BCCM) (Universiteit Gent, K. L. Ledeganckstraat 35, 9000 Gent, Belgium) on Mar. 14 2019 with accession number LMG P-31319 and herein further also indicated as MY02 strain. In another aspect, the combination for use according to the present invention comprises *B. subtilis* and *B. coagulans*, wherein said *B. coagulans* spores are derived from strain MY01 as deposited with the BCCM with accession number LMG P-31318. Said strain has been deposited with the Belgian Co-ordinated Collection of Micro-Organisms (BCCM) (Universiteit Gent, K. L. Ledeganckstraat 35, 9000 Gent, Belgium) on Mar. 14 2019 with accession number LMG P-31318 and herein further also indicated as MY01 strain.

In yet a further aspect, the combination for use according to the present invention comprises *B. subtilis* and *B. coagulans*, wherein said *B. subtilis* spores are derived from strain MY02 as deposited with the BCCM with accession number LMG P-31319 and wherein said *B. coagulans* spores are derived from strain MY01 as deposited with the BCCM with accession number LMG P-31318.

In another aspect, the present invention provides a pharmaceutical composition for use in the prevention and/or treatment of a functional gastro-intestinal disorder in a subject. Said pharmaceutical composition comprises a combination comprising *B. subtilis* and *B. coagulans* spores according to the different embodiments as described above. Said pharmaceutical composition further comprises one or more pharmaceutically acceptable carriers, diluents or excipients. In a further embodiment, the pharmaceutical composition according to this invention is for use in the prevention and/or treatment of a functional gastro-intestinal disorder selected from functional dyspepsia, functional chest pain, functional heartburn, belching disorders, nausea and vomiting disorders, functional abdominal bloating or distension, reflux hypersensitivity, irritable bowel syndrome, functional constipation, functional diarrhea; preferably selected from functional dyspepsia, functional chest pain, functional heartburn, belching disorders, nausea and vomiting disorders, functional abdominal bloating or distension. In an even more preferred embodiment, the pharmaceutical composition according to the invention is for use in the prevention and/or treatment of functional dyspepsia in a subject.

In another embodiment, the present invention discloses a pharmaceutical composition comprising B. subtilis and B. coagulans spores and one or more pharmaceutically acceptable carriers for use as an alternative therapy or adjunct therapy for gastric acid suppression treatment in a subject, in particular in a subject with a functional gastro-intestinal (GI) disorder. Said functional GI disorder is selected from functional dyspepsia, functional chest pain, functional heartburn, belching disorders, nausea and vomiting disorders, functional abdominal bloating or distension, reflux hypersensitivity, irritable bowel syndrome, functional constipation, functional diarrhea. In a further embodiment, said functional GI disorder is selected from functional dyspepsia, functional chest pain, functional heartburn, belching disorders, nausea and vomiting disorders, functional abdominal bloating or distension. Thus, in an even more preferred embodiment, the present invention provides a pharmaceutical composition comprising a combination of B. subtilis and B. coagulans spores for use as an alternative therapy or as an adjunct therapy for gastric acid suppression treatment in a subject, in particular in a subject with a functional gastro-intestinal (GI) disorder.

Further, in one aspect of the invention, a pharmaceutical composition comprising a combination of B. subtilis and B. coagulans spores for use according to all the embodiments of the invention, is provided in combination with a standard therapy for functional gastro-intestinal disorders. In a further aspect, said standard therapy is selected from proton pump inhibitors, acid suppressive therapy (proton pump inhibitors and histamine-2 receptor antagonists), antibiotics, antiemetics, prokinetics, spasmolytics, antidepressants, antipsychotics, digestive enzymes and botanical extracts.

The pharmaceutical composition for use according to the different embodiments of the invention may further comprise one or more ingredients selected from the list comprising plant extracts, such as ginger, artichoke, proteins, vitamins, minerals or digestive enzymes, such as amylase, cellulase, lipase, beta-galactosidase, papain, bromelain and proteases.

In another embodiment, the pharmaceutical composition for use according to the different embodiments of the invention is in the form of a tablet, a capsule, a stick or any other edible form, including but not limited to functional food, juice, drinks or sweets.

In another embodiment, the pharmaceutical composition of the present invention is a product of the dairy industry, beverage industry, food industry, or pharmaceutical industry, or it is a natural product.

In a further aspect of the invention, the combination or pharmaceutical composition according to the different embodiments of the invention is for use in the prevention and/or treatment of functional gastro-intestinal disorders, such as functional dyspepsia, in a subject. Said subject can be a human subject, such as an adult or an infant. In another embodiment, said subject can be animal, preferably a pet or a production animal. Preferably, the subject is a human.

The present invention also provides a B. subtilis strain. Said B. subtilis strain has been deposited with the Belgian Co-ordinated Collection of Micro-Organisms (BCCM) (Universiteit Gent, K. L. Ledeganckstraat 35, 9000 Gent, Belgium) on 14, Mar. 2019, with accession number LMG P-31319. The present invention further also provides a B. coagulans strain. Said B. coagulans strain has been deposited with the Belgian Co-ordinated Collection of Micro-Organisms (BCCM) (Universiteit Gent, K. L. Ledeganckstraat 35, 9000 Gent, Belgum) on 14, Mar. 2019 with accession number LMG P-31318.

In a further aspect, the invention describes the use of Bacillus coagulans or Bacillus subtilis or a combination of both strains to enhance the gastro-intestinal function in a subject. More in particular, the use of a combination comprising B. subtilis and B. coagulans spores to enhance the gastro-intestinal function in a subject is disclosed. Said subject is a human or a mammal; preferably a human subject. In a specific embodiment, said subject is a human with a functional gastro-intestinal disorder; in particular a human with functional dyspepsia. In another embodiment, said subject is a healthy subject.

In a further aspect, and in said use, the B. subtilis and B. coagulans spores are in a 1:1, a 1:2 or a 2:1 ratio present in the combination.

In still another further aspect and in said use, the B. subtilis spores are derived from strain MY02 as deposited with the BCCM with accession number LMG P-31319. In another aspect, and in said use, the B. coagulans spores are derived from strain MY01 as deposited with the BCCM with accession number LMG P-31318.

Another aspect discloses the use of a composition to enhance to gastro-intestinal function in a subject, said composition comprising a combination comprising B. subtilis and B. coagulans spores according to any of the described embodiments, and one or more pharmaceutically acceptable carriers, diluents or excipients. Said composition may further comprise one or more ingredients selected from plant extracts, proteins, vitamins, minerals and digestive enzymes. In another aspect, said composition is in the form of a tablet, capsule, sachet, stick or any other edible form including but not limited to functional food, juice, drinks or sweets. In still another aspect said composition is a product of the dairy industry, beverage industry, or pharmaceutical industry, or is a natural product.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

ES: early satiation; PPF: postprandial fullness; UAB: upper abdominal bloating; UAP: upper abdominal pain; EGB: epigastric burning; NS: nausea; BC: belching; HB: heartburn; FT: fatigue; PPNS: postprandial nausea; PPUAP: postprandial upper abdominal pain.

DETAILED DESCRIPTION OF THE INVENTION

The present invention is based on the discovery that a combination comprising B. subtilis and B. coagulans are particularly useful in the treatment and/or prevention of functional gastro-intestinal disorders, such as functional dyspepsia, and to enhance the gastro-intestinal function in a human. In particular, the inventors found that a combination comprising B. subtilis and B. coagulans spores are useful in the treatment and/or prevention of functional gastro-intestinal disorders, such as functional dyspepsia, in a human. In addition, the combination comprising B. subtilis and B. coagulans spores is also useful to enhance the general gastro-intestinal function, in particular to stimulate the gastro-intestinal digestion and to reduce general complaints of postprandial fullness, upper abdominal bloating or early satiation after having a meal.

Moreover, the inventors have found that the combination comprising B. coagulans and B. subtilis spores reduces symptoms of epigastric pain and burning, chest pain and heartburn. These complaints are often treated by gastric acid suppression therapies such as proton pump inhibitors. Therefore, in a further embodiment, the invention provides a combination or pharmaceutical composition comprising B. coagulans spores and B. subtilis spores according to the different embodiments of the invention that is also for use as an alternative therapy or adjunct therapy for gastric acid suppression treatment such as proton pump inhibitors in a subject; in particular in a subject with functional gastro-intestinal disorder.

The present invention thus provides a combination or pharmaceutical composition comprising B. coagulans and B. subtilis for use in the treatment of functional gastro-intestinal disorders. Further, also the use of said combination or said composition is disclosed to enhance the general gastro-intestinal function, either in a healthy subject, or in a subject with a functional gastro-intestinal disorder, such as functional dyspepsia.

In the context of the present invention, improvement of the gastro-intestinal function is observed either in healthy subjects as well as in subject with a functional gastro-intestinal disorder. Also in the context of the present invention, improvement of the gastro-intestinal function is any improvement that is observed in the activity and functionality of the gastro-intestinal tract. In particular, the gastro-intestinal function is improved after consumption of food, for example evidenced by the reduction of general complaints of postprandial fullness, upper abdominal bloating or early satiation after having a meal. In a particular aspect, the combination or composition according to the different embodiments of the present invention is used to stimulate the gastro-intestinal digestion to reduce occasional digestive symptoms in otherwise healthy subjects like belching, upper abdominal bloating, upper abdominal pain or burning, heartburn, and gastroesophageal reflux.

Bacteria are typically in the form of bacterial spores or as vegetative bacterial cells, or a mixture of both. In a particularly preferred instance in the present invention, the bacteria are in the form of bacterial spores which can germinate in the gastrointestinal tract. In another embodiment, they may have been treated such that they cannot germinate. For example, the spores could be treated by heat and may, for instance, have been subjected to autoclaving to prevent germination. In another embodiment, the bacteria are in the form of vegetative cells. The spores or vegetative cells may, in one embodiment, be provided in isolated form. In yet another embodiment, the microbial material can be extracts of bacterial cells. In still another embodiment, the microbial material can be metabolites of bacterial cells released during cell growth in the culture medium. In another further embodiment, the microbial material can be any combination of bacterial spores, vegetative bacterial cells, extract of bacterial cells or metabolites of bacterial cells. In a preferred embodiment, the bacteria in the different embodiments of the invention are provided as viable spores which can germinate in the gastrointestinal tract.

The formulation or pharmaceutical formulation according to the different embodiments of the invention requires that the bacteria B. subtilis and B. coagulans or their corresponding spores are isolated from eventual growth culture media. The skilled artisan is well aware of the techniques available for isolating the viable bacteria or spores from a growth culture medium such as using centrifugation, filtration, micro manipulation, and the like. For medium and long term storage, the isolated bacteria are preferably maintained in a dry state, such as for example achieve using freeze drying or spray drying. In one embodiment of the invention, the B. subtilis and B. coagulans used in the manufacture of the compositions or pharmaceutical compositions are spray dried B. subtilis and B. coagulans, obtained by spray drying the bacteria using a saccharide protectant, in particular a trehalose as a protectant. An exemplary process suitable for spray drying the bacteria of the present invention is for instance available from Sunny-Roberts and Knorr (Int. Diary J., 19 (2009) 209-214).

Once isolated the B. subtilis and B. coagulans of the present invention can be prepared by any known or otherwise effective method for pharmaceutically formulating or manufacturing the selected product from. Methods for preparing the pharmaceutical compositions according to the present invention can be found in "Remington's Pharmaceutical Sciences", Mid. Publishing Co. Easton, Pa. USA.

For example, the composition or pharmaceutical composition according to the different embodiments of the invention can be formulated along with common excipients, diluents or carriers, and formed into oral tablets, capsules, sprays, or oral liquids (e.g. suspensions, solutions, emulsions), powders or any other suitable dosage form.

Non-limiting examples of suitable and pharmaceutically acceptable excipients, diluents and carrier can be found in "Handbook of Pharmaceutical Excipients", Second Edition, American Pharmaceutical Association, 1994, and may include: fillers and extenders such as starch, sugars, mannitol, and silicic derivatives; binding agents such as carboxymethyl cellulose and other cellulose derivatives, alginates, gelatin, and polyvinyl pyrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as acetyl alcohol, glycerol monostearate, adsorptive carriers such as kaolin and bentonite; carriers such as propylene glycol and ethyl alcohol, and lubricants such as talc, calcium and magnesium stearate, and solid polyethyl glycols.

The combination, composition and pharmaceutical composition according to the invention are primarily suitable for the use in human adults and infants. Though, they are also suitable for use in animals, especially pets and production animals. Examples of these include dogs, cats, rabbits, horses, cows, pigs, goats, sheep and poultry. The term "subject" as used herein therefore includes both humans and animals.

The composition for use according to the present invention can be in the form of a tablet, a capsule, a sachet, a stick or any other edible form including, but not limited to functional food, juice, drinks or sweets. The term "edible form" as used herein is intended to cover all consumable products, especially food products, and it can be solid, jellied or liquid. The term covers both ready-made products and products which are produced using the probiotic composition as a starter alone, or in combination with conventional starters or other probiotics. The food products can for instance be products of the dairy industry or beverage industry. Alternatively, it can be a natural product.

In the present invention, a "dairy product" means any liquid or semisolid milk or whey based product having a varying fat content. The dairy content can be e.g. cow milk, goat milk, sheep milk, skimmed milk, whole milk, milk recombined from powdered milk and whey without any processing, or a processed product, such as yoghurt, curdled milk, curd, sour milk, sour whole milk, butter milk, another sour milk product, such as villi, filling of snack bars, etc. Another important group includes milk beverages, such as whey beverages, fermented milks, condensed milks, infant baby milks, ice-cream; milk-containing food such as sweets.

The products according to the different embodiments of the invention can also be concentrated and used as ingredients. Further, the products can also be dried and used in the form of powder or lyophilizate. The products are also applicable as capsules, pills or tablets. The products can also be used in the preparation of functional food products, health and wellness promoting edible products, or other corresponding products. It may also be in an animal feed. Possible forms are capsules, pills or tablets, for example, manufactured in conventional processes used in the preparation of such a product for example in the pharmaceutical industry. This, the form of each of the food product, food material, and/or the pharmaceutical products, and the animal feed is not particularly limited.

EXAMPLES

The following example illustrates the present invention. The example is not to be construed to limit the claims in any manner whatsoever.

Example 1

Figure 1:
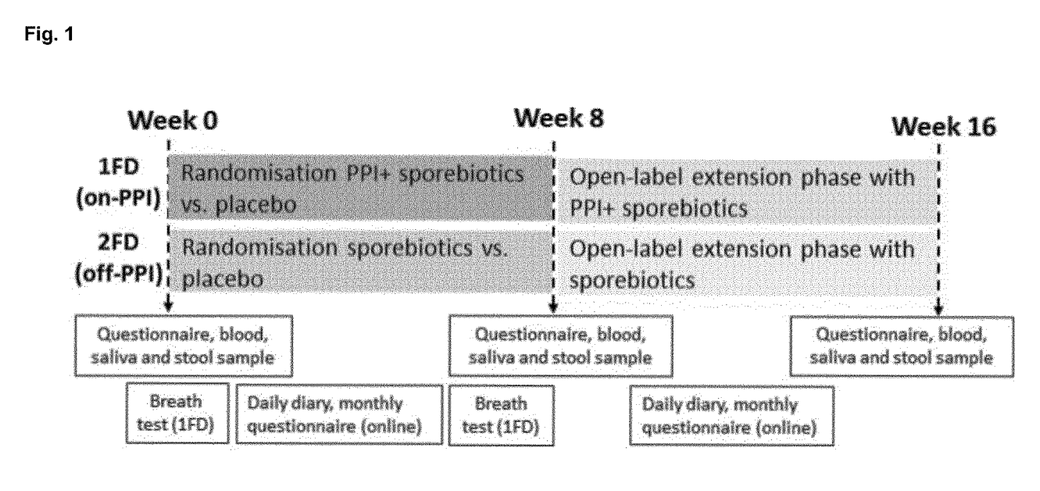
FIG. 1: Study protocol to study the effect of the spore-forming probiotics of the present invention on dyspeptic symptoms and clinical parameters.

I. Study-Setup
Trial Objectives
Our objective is to study the effect of spore-forming probiotics on dyspeptic symptoms and blood, saliva and stool parameters in FD patients with and without acid suppression by proton pump inhibitors (PPI), compared to placebo.
Trial Registration
The study is approved by the Ethics Committee Research KU Leuven (Belgium) and is registered in the ClinicalTrial.gov database under the accession number NCT04030780.
Primary Endpoints
The effect of sporebiotics (combination of *Bacillus coagulans* MY01 and *Bacillus subtilis* MY02 spores) vs. placebo on clinical symptoms, assessed with the LPDS questionnaire.
Secondary Endpoints
The effect of sporebiotics (combination of *Bacillus coagulans* MY01 and *Bacillus subtilis* MY02 spores) vs. placebo on blood, saliva and stool parameters. Exploratory endpoints are the effect of said sporebiotics vs. placebo on bile acid breath tests to assess bacterial overgrowth (cohort 1FD).
Trial Design and Flowchart
A prospective randomized placebo-controlled study in 2 FD cohorts with open-label extension phase is performed (FIG. 1):
 cohort 1FD (on-PPI): study procedures at inclusion (week 0 or week-1) (1) and after 8 weeks on-PPI+ sporebiotics or placebo (2) followed by 8 weeks on-PPI+ sporebiotics (open label);
 cohort 2FD (off-PPI): study procedures at inclusion (week 0 or week-1) (1) and after 8 weeks of sporebiotics or placebo (2) followed by 8 weeks of sporebiotics (open label).

A trial flowchart as displayed in Table 1 was used.

TABLE 1

| Trial flow chart of the study | | | |
|---|---|---|---|
| Study visit (week) | 1 (week 0 or −1) | 2 (week 8) | 3 (week 16) |
| Review in- and exclusion criteria | X | | |
| Review concomitant medication | X | X | X |
| Sign informed Consent | X | | |
| Randomization | X | | |
| Dispense study medication | X | X | |
| Questionnaires | X (online) | X (online) | X (online) |
| Blood, saliva and/or stool sample | X | X | X |
| Breath test (cohort 1FD only) | X | X | |
| LPDS diary | Daily throughout the study | | |

Trial Medication
a) Investigational Medicinal Product and Dosing Regimen
FD patients (on- or off-PPI) are randomized to treatment with spore-forming probiotics or placebo. Spore-forming probiotics in this study is a combination of *Bacillus coagulans* MY01 and *Bacillus subtilis* MY02 and the spore-forming probiotics are administered as 1 capsule twice daily ($2.5 \times 10^9$ CFU per capsule; 50:50 ratio) during 8 weeks. Placebo treatment is administered in similar capsules and also administered twice daily. During the open-label extension phase, sporebiotics are given for a further 8 weeks.
b) Drug Accountability
Remaining capsules are counted every 8 weeks.
c) Subject Compliance
Patients are contacted by email every month to verify compliance.
d) Concomitant Medication (non-IMP)

Patients are requested to refrain from concomitant forbidden medication.

Selection and Withdrawal of Subjects a) Inclusion Criteria

Patients are eligible for the study if all of the following criteria are met:

Patients >18 years with FD diagnosis (Rome IV criteria):
  epigastric pain or burning 1 or more days per week (EPS)
  postprandial fullness or early satiation severe enough to impact on regular activities for 3 or more days per week (PDS)
FD cohort 1: daily PPI-treatment during the last 4 weeks (any type and dose)
FD cohort 2: No PPI-treatment during the last 8 weeks
Male or female (not pregnant or lactating and using contraception or postmenopausal)
Normal bowel habits (defecation once every 3 days up to 3 times a day)
Witnessed written informed consent
Access to home freezer (−18 to −20° C.)
Capable to understand and comply with the study requirements b) Exclusion Criteria Patients are excluded from the study if any of the following criteria are met:

Any active somatic or psychiatric condition that may explain dyspeptic symptoms (stable dose of single antidepressant allowed for psychiatric indication, no limitation for other indications)
Predominant symptoms of gastro-esophageal reflux disease (GERD) or irritable bowel syndrome (IBS)
Use of immunosuppressants or antibiotics <3 months
History of major abdominal surgery (except for appendectomy, cholecystectomy or splenectomy)
Personal history of diabetes mellitus type 1, celiac disease or inflammatory bowel disease
Diabetes mellitus type 2 (including therapy)
Active malignancy (including therapy)
Known HIV, HBV or HCV infection (including therapy)
Magnetizable objects (e.g. cochlear implants, neural stimulator, pacemaker, metal fragments or implants) or claustrophobia (MRI safety criteria with additional consent form in cohort 2FD only, other procedures can still take place)
Significant alcohol use (>10 units/weeks)

c) Selection of Participants

FD patients are recruited at the outpatient clinic of general and functional GI disorders or at the endoscopy unit. Advertisements are distributed via the magazine 'Metro' and hung as posters in the hospital and university, which are also uploaded under 'oproep studies' on the UZ Leuven intranet website. Patients replying to this advertisement are invited for a study visit. Patients can also be recruited from referring hospitals if all inclusion and no exclusion criteria are fulfilled.

d) Randomization Procedure

The randomization list between sporebiotics and placebo is done by the sponsor using an online randomization tool (www.randomization.com) with block sizes of 5. The randomization list is kept by the sponsor for both cohort 1 FD and 2FD. The study treatment is numbered according to the randomization list and provided by the sponsors to the investigators who remain blinded for the randomization code.

e) Withdrawal of Subjects

The patient has the right to withdraw from the study at any time, without affecting future management and treatment. The patient may be withdrawn from the study if:

The patient experiences any untoward event that the investigator considers detrimental to the well-being of the patient
The patient violates the eligibility criteria of the study protocol
The patient starts treatment with forbidden concomitant medication
The patient is non-compliant with the required study procedures, e.g. filling out the intake or follow-up (monthly) questionnaires Depending on the performed procedures and the filled out questionnaires, data of a patient withdrawing from the study can still be used.

f) Expected Duration of Trial

The duration of the study is 16 weeks. The duration of the complete trial from the first visit of the first patient to the last visit of the last patient is expected to be 24 months.

LPDS Diary

Throughout the study, subjects filled out the Leuven Postprandial Distress Scale (LPDS) on a daily basis. This LPDS diary has been validated for dyspeptic and heart burn symptoms assessment (Carbone et al, 2016; Aliment Pharmacol Ther 44:989-1001). The LPDS scale is a diary instrument which consists of 10 upper abdominal symptoms (early satiation, postprandial fullness, upper abdominal bloating, upper abdominal pain, epigastric burning, nausea, belching, heartburn, postprandial nausea, postprandial epigastric pain) and fatigue as an additional quality of life parameter. The rating of items is expressed as verbal descriptors (five levels per item, ranging from absent to very sever) accompanied by 'smiley faces'(☺ - ☹). See Table 2 for an example of the LPDS diary. For analysis, verbal descriptors are converted to numerical values as follows: absent=0; mild=1; moderate=2; severe=3; and very severe=4.

TABLE 2

Example of the LPDS diary questions. The daily questionnaire consisted of 10 questions addressing upper abdominal symptoms and one question addressing general fatigue as quality of life parameter.

1. How hard was it for you to finish a normal meal today because you felt full too quickly?
Absent ☺ Mild ☺ Moderate ☺ Severe ☹ Very severe ☹

2. How bad was the feeling today that your food was on your stomach?
Absent ☺ Mild ☺ Moderate ☺ Severe ☹ Very severe ☹

3. How much did you suffer from feeling bloated in your stomach today?
Absent ☺ Mild ☺ Moderate ☺ Severe ☹ Very severe ☹

4. How much did you suffer from pain in your stomach area today?
Absent ☺ Mild ☺ Moderate ☺ Severe ☹ Very severe ☹

TABLE 2-continued

Example of the LPDS diary questions. The daily questionnaire consisted of 10 questions addressing upper abdominal symptoms and one question addressing general fatigue as quality of life parameter.

5. How much did you suffer from a burning feeling in your stomach area today?
Absent ☺  Mild ☺  Moderate ☺  Severe ☹  Very severe ☹
6. How much did you suffer from nausea (feeling sick) today?
Absent ☺  Mild ☺  Moderate ☺  Severe ☹  Very severe ☹
7. How much did you suffer from troublesome burping today?
Absent ☺  Mild ☺  Moderate ☺  Severe ☹  Very severe ☹
8. How much did you suffer from a burning feeling behind your breastbone (in your chest) today?
Absent ☺  Mild ☺  Moderate ☺  Severe ☹  Very severe ☹

II. Results

At this stage, results of the study are available for the open label phase only, and for a limited number of patients. The study is currently still ongoing and more patients are to be recruited and data are further analysed. Nevertheless, the currently available data already show the positive effects of the combination comprising *B. subtilis* and *B. coagulans* for the prevention and/or treatment of functional gastro-intestinal disorders.

Seven days (week-1) before the start (week 0) of the placebo-controlled, randomized blinded phase of the trial, patients started to record their gastrointestinal symptoms on a daily basis in the LPDS diary. The LPDS diary was completed throughout the entire clinical trial (blinded phase followed by open label phase). The average results of the daily recordings during week-1 are considered as the baseline values per symptom. After completion of the blinded phase in which 8 weeks placebo or 8 weeks sporebiotics (combination of *Bacillus coagulans* MY01 and *Bacillus subtilis* MY02 spores) were administered as trial medication, patients enrolled in the open label phase, wherein all patients were supplemented daily with the sporebiotics (combination of *Bacillus coagulans* MY01 and *Bacillus subtilis* MY02 spores).

Figure 2:
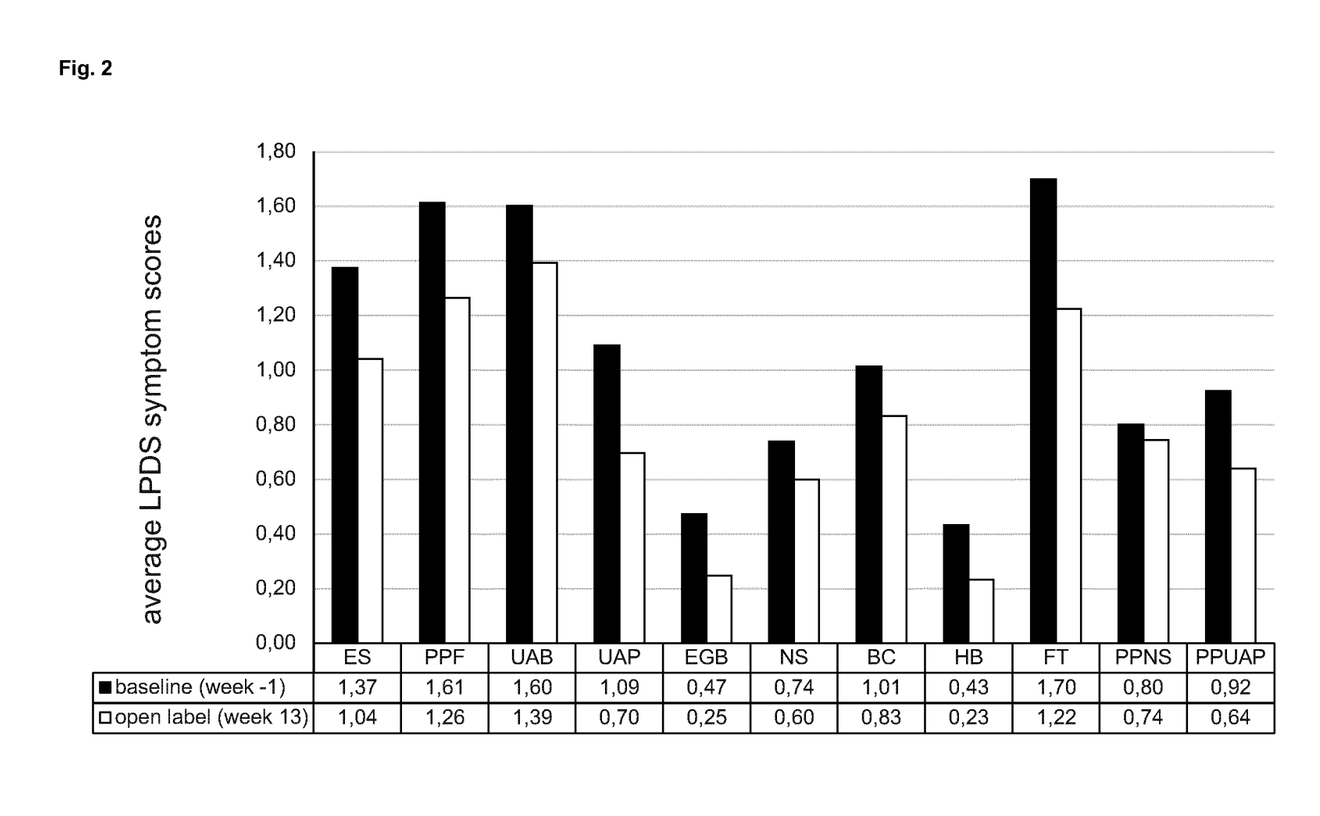
FIG. 2 Average LPDS scores reported by cohort 1FD (on-PPI) at baseline (1 week before start of the blinded phase) and during week 13. Week 13 corresponds to the $5^{th}$ week of the open label phase, wherein all patients received sporebiotics of the present invention (2 capsules per day). ES: early satiation; PPF: postprandial fullness; UAB: upper abdominal bloating; UAP: upper abdominal pain; EGB: epigastric burning; NS: nausea; BC: belching; HB: heartburn; FT: fatigue; PPNS: postprandial nausea; PPUAP: postprandial upper abdominal pain.

FIG. 2 shows the baseline symptom values of week-1, compared to the most recently available average LPDS scores, reported by 18 patients of cohort 1FD (on-PPI) during week 13 of the trial, which corresponds to week 5 of the open-label phase. The severity of all dyspeptic symptoms was clearly decreased in cohort 1FD (on-PPI) during week 13 of the trial, except for the postprandial nausea (PPNS).

Unexpectedly, the gastric-acid related symptoms epigastric burning (EGB) and heartburn (HB) were reduced by almost 50%. Since in the cohort 1FD gastric acid suppressive therapy (proton pump inhibitors PPI) is combined with administration of the sporebiotics of the present invention, epigastric burning and heartburn were expected to be rare symptoms in this population, because of the PPI therapy. However, dyspepsia patients seem still to suffer from these bothersome symptoms even though they receive PPI therapy. Remarkedly, administration of the sporebiotics of the present invention further reduced the symptoms of epigastric burning an heartburn. These data thus show that the combination of *B. coagulans* and *B. subtilis* sporebiotics ameliorates functional gastrointestinal symptoms when said sporebiotics are administered in combination with PPIs. As such, the current data provide sufficient evidence that the combination of *B. coagulans* and *B. subtilis* sporebiotics can be used in the treatment of functional gastro-intestinal disorders, as well as an adjunct therapy in combination with PPIs for dyspeptic symptoms.

Figure 3:
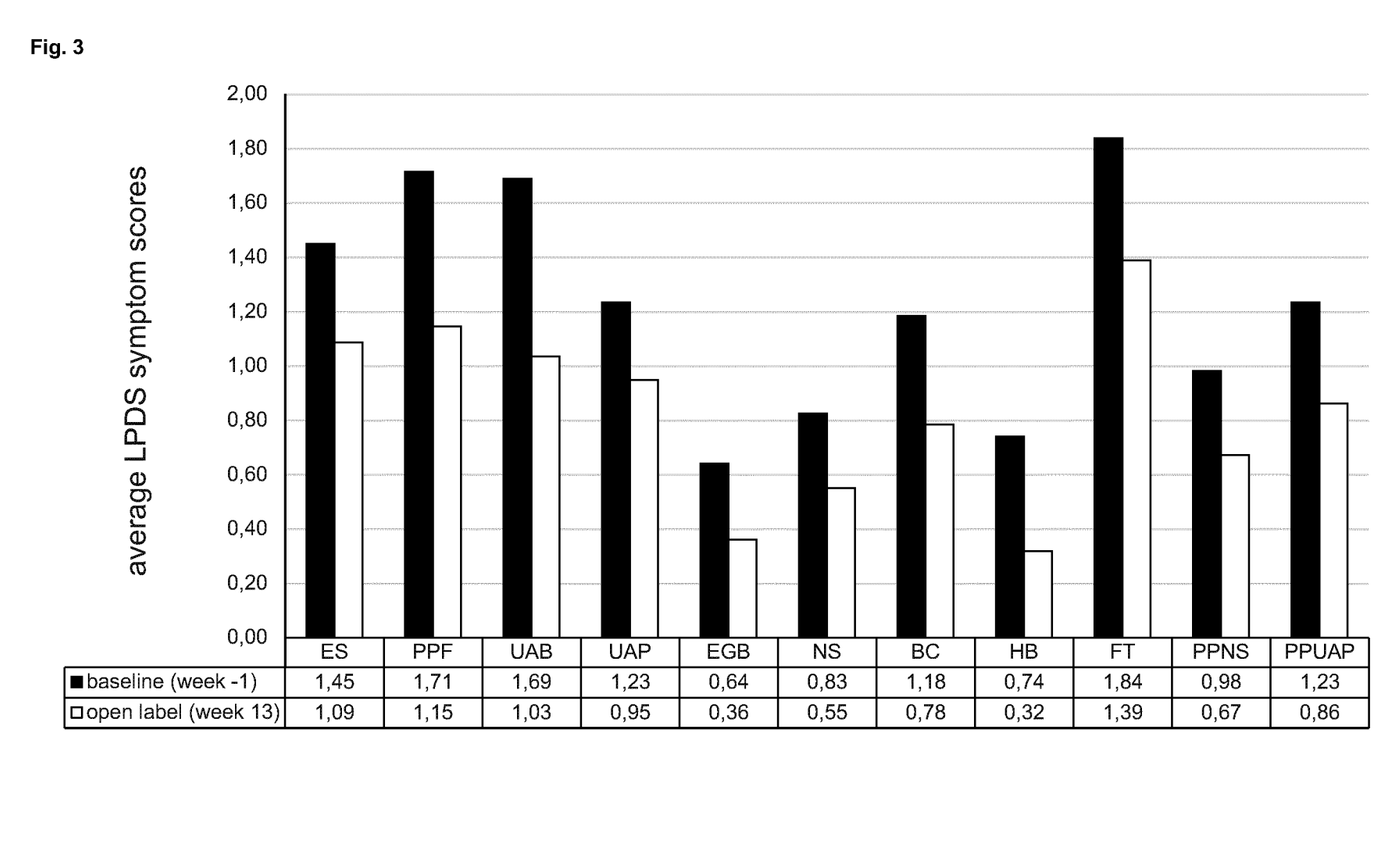
FIG. 3 Average LPDS scores reported by cohort 2FD (off-PPI) at baseline (1 week before start of the blinded phase) and during week 13. Week 13 corresponds to the $5^{th}$ week of the open label phase, wherein all patients received sporebiotics of the present invention (2 capsules per day).

FIG. 3 shows the baseline symptom values of week-1 compared to the most recently available average LPDS scores reported by 16 patients of cohort 2FD (off-PPI) during week 13 o the trial, which corresponds to week 5 of the open label phase. At week 13 of the trial, the severity of all dyspeptic symptoms was markedly decreased in cohort 2FD (off-PPI) as compared to the start point (week-1) of the study. These data thus show that the combination of *B. coagulans* and *B. subtilis* spores is an effective treatment for functional gastro-intestinal disorders without additional types of therapy.

Figure 4:
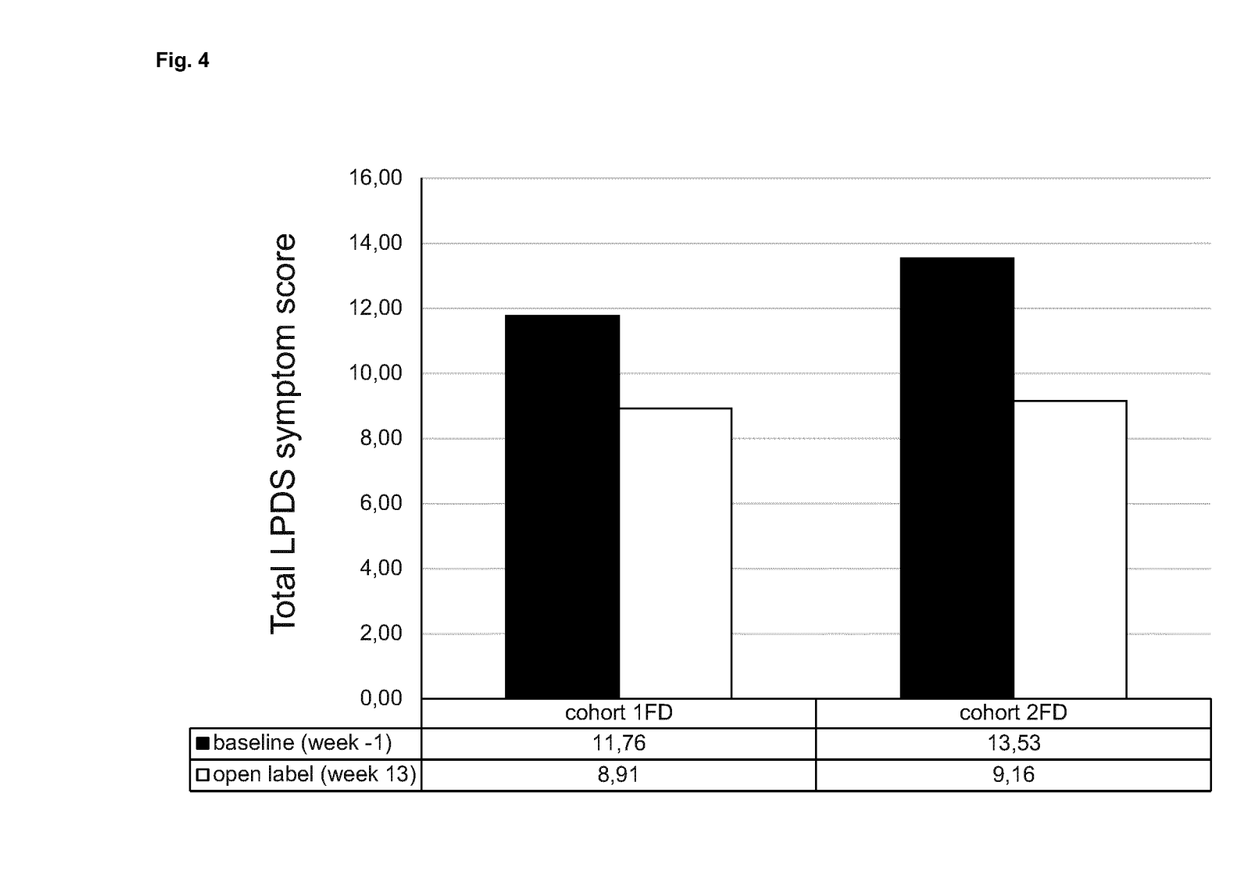
FIG. 4 Sum of average LPDS scores at baseline and during week 13 for cohorts 1FD and 2FD. Week 13 corresponds to the $5^{th}$ week of the open label phase, wherein all patients received sporebiotics of the present invention (2 capsules per day). ES: early satiation; PPF: postprandial fullness; UAB: upper abdominal bloating; UAP: upper abdominal pain; EGB: epigastric burning; NS: nausea; BC: belching; HB: heartburn; FT: fatigue; PPNS: postprandial nausea; PPUAP: postprandial upper abdominal pain.

FIG. 4 shows for both cohorts 1FD and 2FD the total sum of the average baseline symptom scores (week-1 at start), compared to the total sum of the average LPDS scores reported during week 13 of the trial. The presented data show that the combination of *B. coagulans* and *B. subtilis* spores clearly reduces all dyspeptic symptoms (questioned in the LPDS diary) combined with the symptom of fatigue in patients undergoing additional acid suppressive therapy (on-PPI) as well as in patients without additional treatment (off-PPI).

The invention claimed is:

1. A method for treating a functional gastroduodenal disorder in a subject in need thereof, the method comprising administering to the subject a combination comprising *Bacillus subtilis* spores and *Bacillus coagulans* spores,
   wherein the *B. subtilis* spores are derived from strain MY02 as deposited with Belgian Co-ordinated Collection of Micro-Organisms (BCCM) with accession number LMG P-31319, and
   wherein the *B. coagulans* spores are derived from strain MY01 as deposited with the BCCM with accession number LMG P-31318.

2. The method according to claim 1, wherein the functional gastroduodenal disorder is selected from the group consisting of functional dyspepsia, functional chest pain, functional heartburn, belching disorder, nausea and vomiting disorders, functional abdominal bloating, and distension.

3. The method according to claim 2, wherein the functional gastroduodenal disorder is functional dyspepsia.

4. The method according to claim 3, wherein said *B. subtilis* and *B. coagulans* spores are in a 1:1, a 1:2, or a 2:1 ratio.

5. A method of treating a functional gastroduodenal disorder in a subject in need thereof, the method comprising administering to the subject a pharmaceutical composition comprising:
   *B. subtilis* spores derived from strain MY02 as deposited with the BCCM with accession number LMG P-31319;
   *B. coagulans* spores derived from strain MY01 as deposited with the BCCM with accession number LMG P-31318; and one or more pharmaceutically acceptable carriers, diluents, or excipients.

6. The method according to claim 5, wherein the functional gastroduodenal disorder is selected from the group consisting of functional dyspepsia, functional chest pain, functional heartburn, belching disorder, nausea and vomiting disorders, functional abdominal bloating, and distension.

7. The method according to claim 6, wherein the functional gastroduodenal disorder is functional dyspepsia.

8. The method according to claim 5, wherein said pharmaceutical composition further comprises one or more ingredients selected from plant extracts, proteins, vitamins, minerals and digestive enzymes.

9. The method according to claim 5, wherein said pharmaceutical composition is in the form of a tablet, capsule, sachet, stick, functional-food, juice, drink, or sweets.

10. The method according to claim 5, wherein said pharmaceutical composition is a product of dairy industry, beverage industry, or pharmaceutical industry.

11. The method according to claim 1, wherein the subject is a human or an animal.

12. The method according to claim 1, further comprising administering to the subject an additional therapy for the treatment and/or prevention of functional gastroduodenal disorders.

13. Method according to claim 12, wherein the additional therapy for the treatment and/or prevention of functional gastroduodenal disorders is selected from the group consisting of acid suppressive therapy, antibiotics, antiemetics, prokinetics, spasmolytics, antidepressants, antipsychotics, digestive enzymes, and botanical extracts.

\* \* \* \* \*